United States Patent
Altman et al.

(10) Patent No.: US 10,238,770 B2
(45) Date of Patent: *Mar. 26, 2019

(54) REPARATIVE CELL ISOLATION AND DELIVERY

(71) Applicants: Board of Regents, The University of Texas System, Austin, TX (US); Ingeneron, Inc., Houston, TX (US)

(72) Inventors: Andrew M Altman, Temple, TX (US); Eckhard U. Alt, Houston, TX (US); Michael E. Coleman, The Woodlands, TX (US)

(73) Assignees: Ingeneron, Inc., Houston, TX (US); Board of Regents, The university of Texas System, Austin, TX (US)

( * ) Notice: Subject to any disclaimer, the term of this patent is extended or adjusted under 35 U.S.C. 154(b) by 28 days.

This patent is subject to a terminal disclaimer.

(21) Appl. No.: 14/930,541

(22) Filed: Nov. 2, 2015

(65) Prior Publication Data
US 2016/0051729 A1    Feb. 25, 2016

Related U.S. Application Data

(63) Continuation of application No. 12/766,757, filed on Apr. 23, 2010, now Pat. No. 9,173,975.

(Continued)

(51) Int. Cl.
*A61L 27/36* (2006.01)
*A61L 27/24* (2006.01)
(Continued)

(52) U.S. Cl.
CPC .......... *A61L 27/3604* (2013.01); *A61L 27/18* (2013.01); *A61L 27/20* (2013.01); *A61L 27/24* (2013.01); *A61L 27/3662* (2013.01); *A61L 27/3679* (2013.01); *A61L 27/38* (2013.01); *C12N 5/0667* (2013.01); *A61K 35/12* (2013.01);
(Continued)

(58) Field of Classification Search
None
See application file for complete search history.

(56) References Cited

U.S. PATENT DOCUMENTS 5,827,937 A    10/1998   Agerup
6,777,231 B1   8/2004    Katz et al.
(Continued)

FOREIGN PATENT DOCUMENTS

WO    2005/113780 A1    12/2005
WO    2007/009036 A1    1/2007
WO    2008/002063       1/2008

OTHER PUBLICATIONS

Altman, AM & Alt, EA "Cell-Assisted Lipotransfer for Cosmetic Breast Augmentation: Supportive Use of Adipose-Derived Stem/Stromal Cells" Aesth Plast Surg 32 (2008) 56-57.
(Continued)

*Primary Examiner* — David W Berke-Schlessel
(74) *Attorney, Agent, or Firm* — Blank Rome LLP

(57) ABSTRACT

Methods are described for generating autologous tissue grafts, including generating grafts at the point of care, which include isolated cell populations that are enriched with stem cells and are mixed with biological fillers including hyaluronic acid and derivatives thereof. The hyaluronic acid localizes the cells to a desired injection site and stimulates collagen production thus enhancing the viability and the longevity of the graft.

14 Claims, 7 Drawing Sheets

Related U.S. Application Data

(60) Provisional application No. 61/172,488, filed on Apr. 24, 2009.

(51) Int. Cl.
  *A61L 27/20* (2006.01)
  *A61L 27/18* (2006.01)
  *A61L 27/38* (2006.01)
  *C12N 5/0775* (2010.01)
  *A61K 35/12* (2015.01)

(52) U.S. Cl.
  CPC ....... *A61L 2300/64* (2013.01); *A61L 2400/06* (2013.01); *A61L 2430/10* (2013.01); *A61L 2430/22* (2013.01); *C12N 2533/80* (2013.01)

(56) References Cited

U.S. PATENT DOCUMENTS

| | | |
|---|---|---|
| 7,157,080 B2 | 1/2007 | Radice et al. |
| 7,595,043 B2 | 9/2009 | Hedrick et al. |
| 2007/0122392 A1 | 5/2007 | Gerecht-Nir et al. |
| 2008/0193536 A1 | 8/2008 | Khademhosseini et al. |
| 2009/0023631 A1 | 1/2009 | Lorenc et al. |
| 2010/0124563 A1 | 5/2010 | Coleman et al. |
| 2010/0285588 A1 | 11/2010 | Stubbers et al. |

OTHER PUBLICATIONS

Altman, AM et al., "Dermal matrix as a carrier for in vivo delivery of human adipose-derived stem cells," Biomaterials, 29 (2008) 1431-1442.

Alvarez, P D-A, et al. "A new bronchoscopic treatment of tracheomediastinal fistula using autologous adipose derived stem cells" Thorax 63 (2008) 374-376.

Bai et al., "Electrophysiological properties of human adipose tissue-derived stem cells," Am. J. Physiol Cell Physiol., 293 (2007) C1539-C1550.

Black, L, et al; "Effect of Adipose-Derived Mesenchymal Stem and Regenerative Cells on Lameness in Dogs with Chronics Osteoarthritis of the Coxofemoral Joint: A Randomized, Double-Blinded, Multicenter, Controlled Trial" Veterinary Therapeutics 8 (2007) 272-284.

Boquest, AC, et al. Isolation and Transcription Profiling of Purified Uncultured Human Stromal Stem Cells: Alteration of Gene Expression after In Vitro Cell Culture. Molecular Biol. of the Cell 16 (2005) 1131-1141.

Bunnell, BA et al. Differentiation of Adipose Stem Cells, Chapter 12, Methods in Molecular Biology 456 (2008) 155-171.

Butler CE. The role of bioprosthetics in abdominal wall reconstruction. Clin Plast Surg. 33(2) (2006) 199-211.

Carruthers A, Carruthers J. Non-animal-based hyaluronic acid fillers: scientific and technical considerations. Plast Reconstr Surg 120(6 Suppl) (2007) 33S-40S.

Chambers, TJ.; "Fusion of Hamster Macrophages Induced by Lectins." Journal of Pathology 123 (1977) 53-61.

Chen, P-Y, et al. "Hyaluronan preserves the proliferation and differentiation potentials of long-term cultured murine adipose-derived stromal cells" Biochemical and Biophysical Research Communications 360 (2007) 1-6.

Cowan et al., "Adipose-derived adult stromal cells heal critical-size mouse calvarial defects," Nat. Biotechnol. 22 (2004) 560-567.

Dominici et al, "Minimal criteria for defining multipotent mesenchymal stromal cells. The International Society for Cellular Therapy position statement.," Cytotherapy 8 (2006) 315-317.

Fagien S, et al. A brief overview and history of temporary fillers: evolution, advantages, and limitations. Plast Reconstr Surg. 120(6 Suppl) (2007) 8S-16S.

Flynn, L et al. "Adipose tissue engineering in vivo with adipose-derived stem cells on naturally derived scaffolds" Journal of Biomedical Materials Research Part A vol. 89A (4) (2009) 929-941.

Gensanne D, et al. "In vivo visualization of hyaluronic acid injection by high spatial resolution T2 parametric magnetic resonance images" Skin Research and Technology 13 (2007) 385-389.

Gerecht, S, et al. "Hyaluronic acid hydrogel for controlled self-renewal and differentiation of human embryonic stem cells" PNAS 104 (27) (2007) 11298-11303.

Gimble J, et al. Adipose-derived adult stem cells: isolation, characterization, and differentiation potential. Cytotherapy 5(5) (2003) 362-9.

Hemmrich, K, et al. "Autologous In Vivo Adipose Tissue Engineering in Hyaluronan-Based Gels—a Pilot Study" Journal of Surgical Research 144 (2008) 82-88.

Katz et al. Emerging approaches to the tissue engineering of fat Clin Plast Surg. 26(4) (1999) 587-603.

Lendeckel et al., "Autologous stem cells (adipose) and fibrin glue used to treat widespread traumatic calvarial defects: case report," J. Craniomaxillofac. Surg. 32 (2004) 370-373.

Lu et al., "Improved viability of random pattern skin flaps through the use of adipose-derived stem cells," Plast. Reconstr. Surg. 121 (2008) 50-58.

Moseley, TA, et al. "Adipose-derived Stem and Progenitor Cells as Filler in Plastic and Reconstructive Surgery" Plast. Reconstruct. Surg. 118 (Suppl.) (2006) 121-128S.

Ogawa, R; "The Importance of Adipose-Derived Stem Cells and Vascularized Tissue Regeneration in the Field of Tissue Transplantation." Current Stem Cell Research & Therapy 1 (2006) 13-20.

Park, Si-Nae, et al.; "Characterization of porous collagen/hyaluronic acid scaffold modified by 1-ethyl-3-(3-dimethylaminopropyl)carbodiimide cross-linking." Biomaterials 23 (2002) 1205-1212.

Parker, AM & Katz, AJ. "Adipose-derived Stem Cells for the Regeneration of Damaged Tissues" Expert Opin. Biol. Ther. 6(6) (2006) 567-578.

Rigotti, G. et al; "Clinical Treatment of Radiotherapy Tissue Damage by Lipoaspirate Transplant: A Healing Process Mediated by Adipose-Derived Adult Stem Cells." Plastic and Reconstructive Surgery 119 (2007) 1409-1422.

Rodbell, "Metabolism of isolated fat cells: Effects of hormones on glucose metabolism and lipolysis" J. Biol. Chem. 239 (1964) 375-380.

Safford et al. "Neurogenic differentiation of murine and human adipose-derived stromal cells," Biochem. Biophys. Res. Commun. 294 (2002) 371-379.

Tholpady SS, et al. "Adipose Tissue: Stem Cells and Beyond" Clin Plastic Surg 33 (2006) 55-62.

Wang et al., "In vivo stimulation of de novo collagen production caused by cross-linked hyaluronic acid dermal filler injections in photodamaged human skin," Arch. Dermatol. 143 (2007) 155-163.

Weigel, T, et al. "Design and Preparation of Polymeric Scaffolds for Tissue Engineering" Expert Rev. Med. Devices 3(6) (2006) 835-851.

Zuk, P; et al; "Multilineage Cells from Human Adipose Tissue: Implications for Cell-Based Therapies." Tissue Engineering 7 (2001) 211-228.

Zuk et al., "Human Adipose Tissue is a Source of Multipotent Stem Cells" Mol. Biol. Cell 13 (2002) 4279-4295.

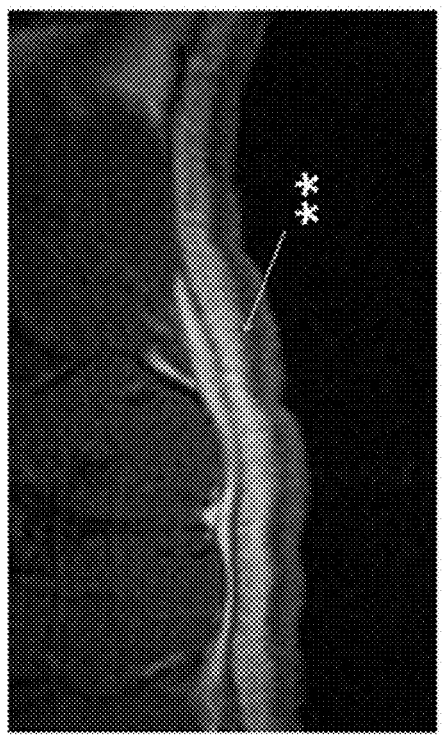
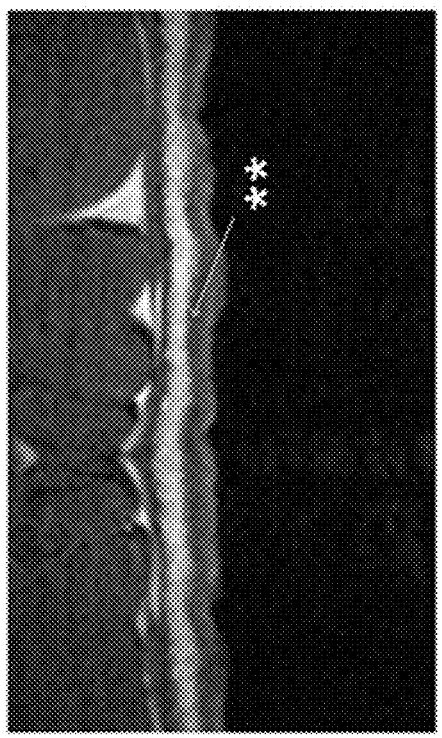
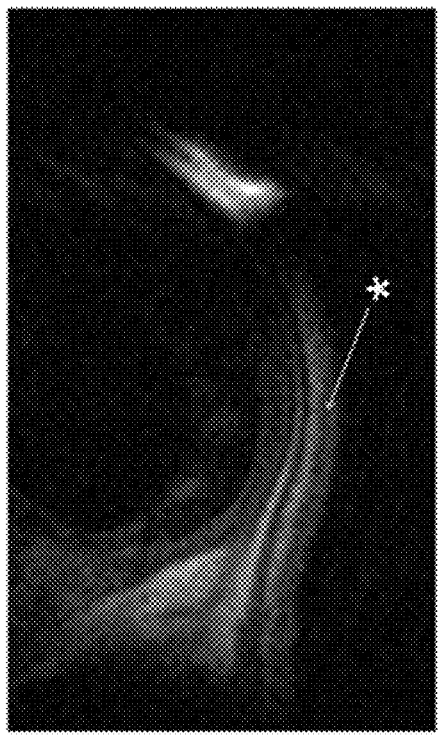
*Figure 2A* Baseline Prior to Photoaging
*Figure 2B* 4 weeks UVB Narrow-Spectrum Photoaging

REPARATIVE CELL ISOLATION AND DELIVERY

CROSS-REFERENCE TO RELATED APPLICATIONS

This application is a continuation of and claims priority to U.S. application Ser. No. 12/766,757, filed on Apr. 23, 2010, published as US 2011/0070281 on Mar. 24, 2011, and issuing on Nov. 3, 2015 as U.S. Pat. No. 9,173,975, which in turn claims priority to U.S. Provisional Patent Application Ser. No. 61/172,488, filed on Apr. 24, 2009, all of which are incorporated herein by reference in their entireties.

FIELD OF THE INVENTION

This invention relates to compositions and methods for delivery of reparative and regenerative cell populations in the treatment of tissue injuries and defects.

BACKGROUND OF THE INVENTION

Without limiting the scope of the invention, its background is described in connection with novel compositions and methods for therapeutic delivery of reparative cell populations in the treatment of soft tissue loss and disfigurement due to pathologic, traumatic, and aging-related processes. Scaffold-based biocompatible prosthetic grafts have been used with some success for restoring soft tissue loss. See e.g. Butler, C. E. The role of bioprosthetics in abdominal wall reconstruction. *Clin. Plast. Surg.* 33 (2006) 199-211. Despite the availability of biocompatible grafts, functional restoration of compromised tissues and organs presents an ongoing challenge in medicine.

Coinciding with advances in both materials-based and cell-based therapeutics for injectable soft tissue augmentation, advances in stem cell biology have provided potential tools for treatment in a variety of settings. In particular, findings that tissue regenerative stem cells can be obtained from adult tissues have made autologous transplantation a possibility. Following this, findings that stem cells can be obtained from tissues other than bone marrow have made autologous transplantation a practicable solution for treatment of other than the most dire conditions. Adipose tissue has emerged as a particularly desirable source of stem cells.

However, practical application of the above mentioned advances has heretofore been unavailable for various reasons to be explained in more detail in the context of the solutions provided herein.

BRIEF SUMMARY OF THE INVENTION

The present invention is directed to methods of treating tissue defects by isolating autologous cell populations enriched in regenerative cells and mixing the isolated autologous cell populations with hyaluronic acid (HA) and/or a hyaluronic acid derivative (HAD) to provide a HA or HAD stabilized autologous cell graft, which then can be injected into the tissue defect. A non-limited group of tissue defects that can be treated with the HA or HAD stabilized autologous cell graft disclosed herein includes wounds, burns, bone fractures, cosmetic defects, cartilage damage, tendon damage, ulcers, fistulas, hernias, retinal degeneration, treatment of ischemic disease, nerve injury, aneurysms, bladder wall repair, intestinal injury, arthritis and vascular vessel repair.

In one aspect, a HA or HAD stabilized autologous cell graft is provided that is generated at a point-of-care and is implanted into a mammalian patient without culturing the autologous cell population. In other embodiments, the autologous cell population is incubated with inductive media before, during or after being mixed with the hyaluronic acid (HA) and/or a hyaluronic acid derivative (HAD). The inductive media can be adapted for generation of one or more of adipocytes, chondrocytes, endothelial cells, hepatocytes, myoblasts, neurons, and osteoblasts.

BRIEF DESCRIPTION THE DRAWINGS

For a more complete understanding of the present invention, including features and advantages, reference is now made to the detailed description of the invention along with the accompanying figures:

FIG. 2A depicts an MRI of a control mouse dorsal skin tissue. FIG. 2B depicts mouse dorsal skin tissue after UVB treatment.

Figure 3A:
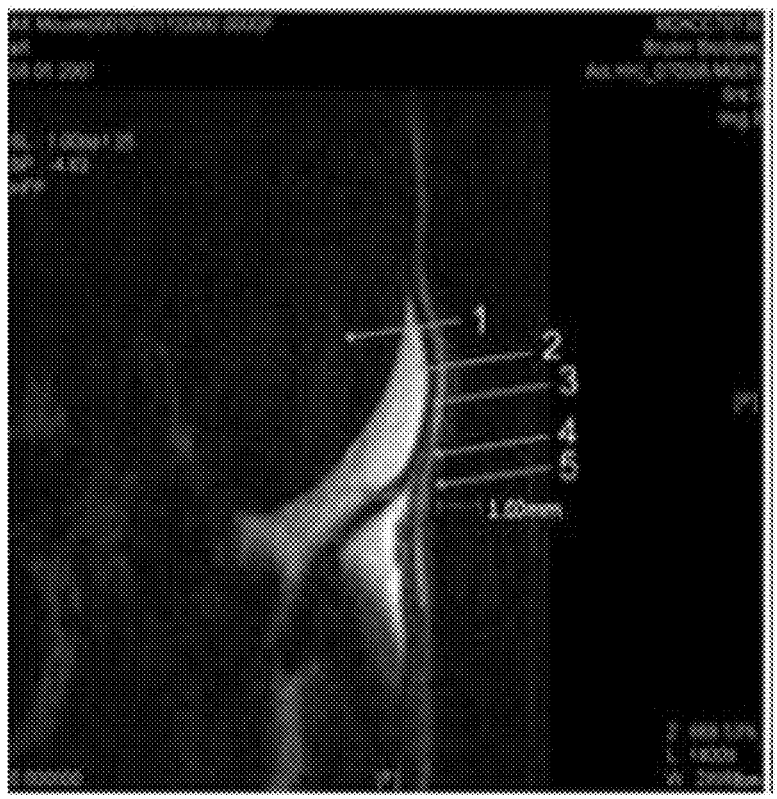
Figure 3B:
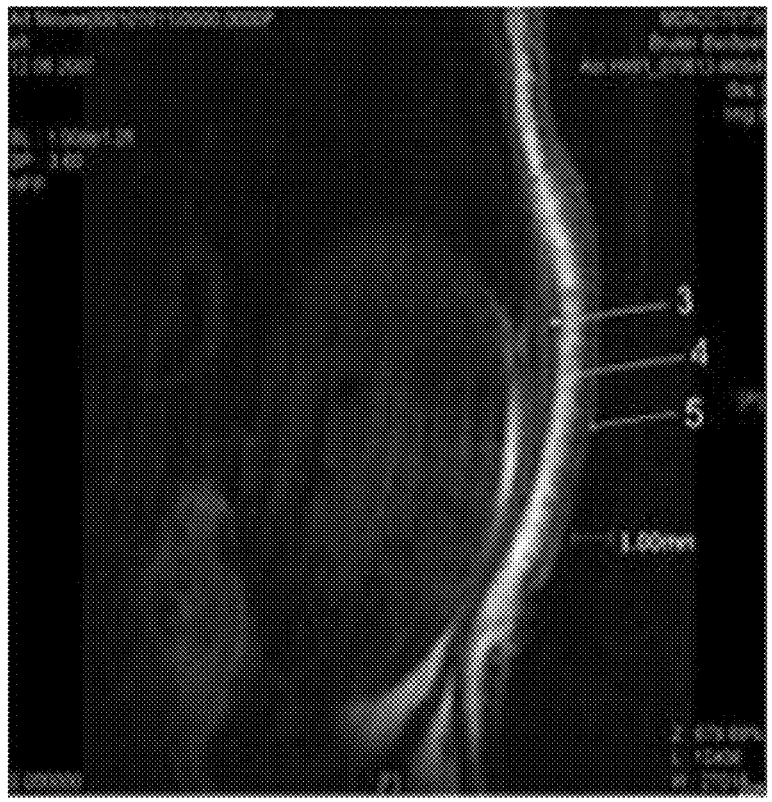
Figure 3C:
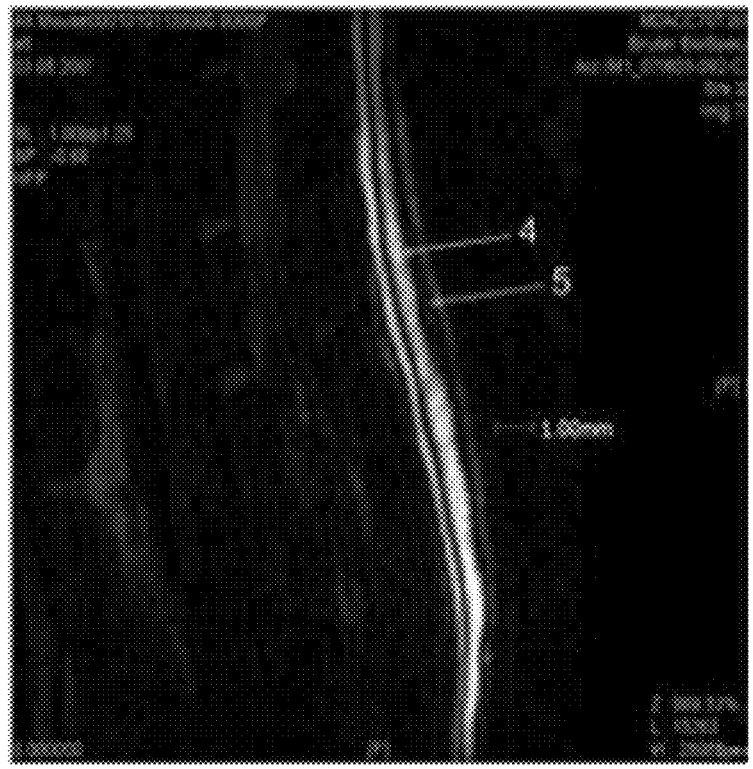
Figure 3D:
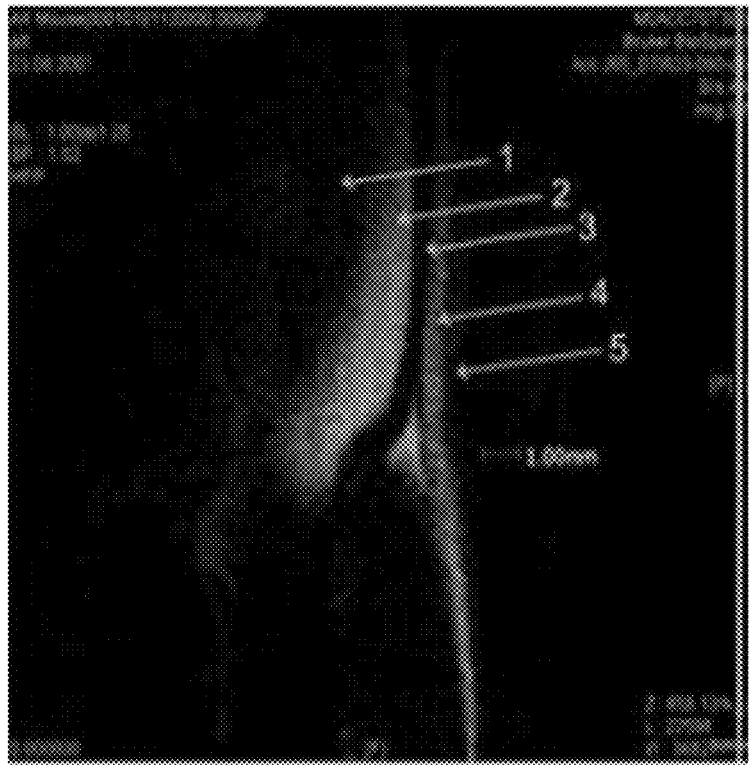
Figure 3E:
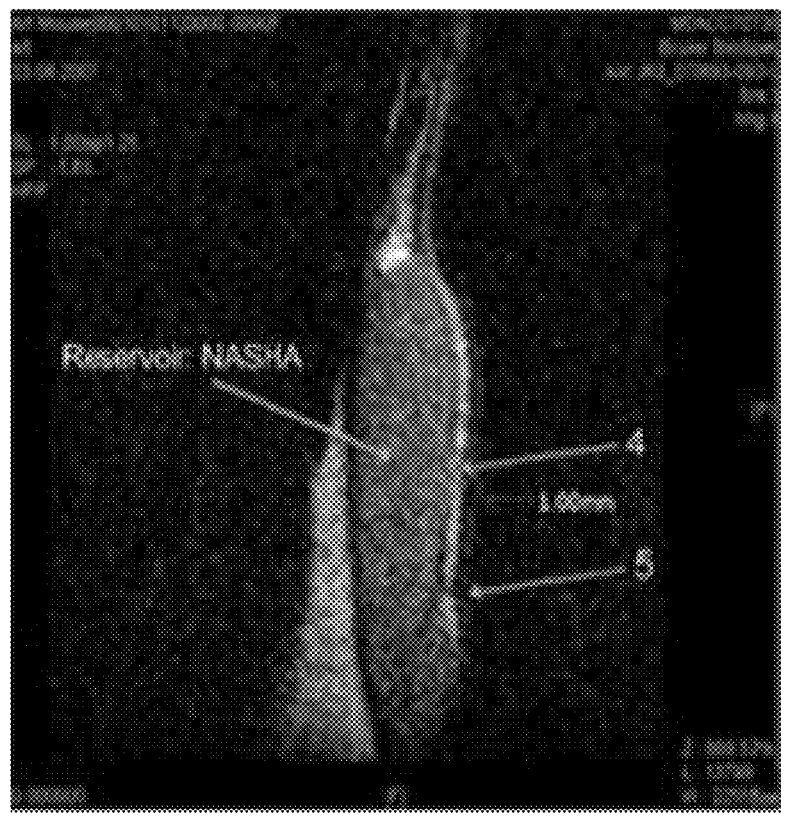
Figure 3F:
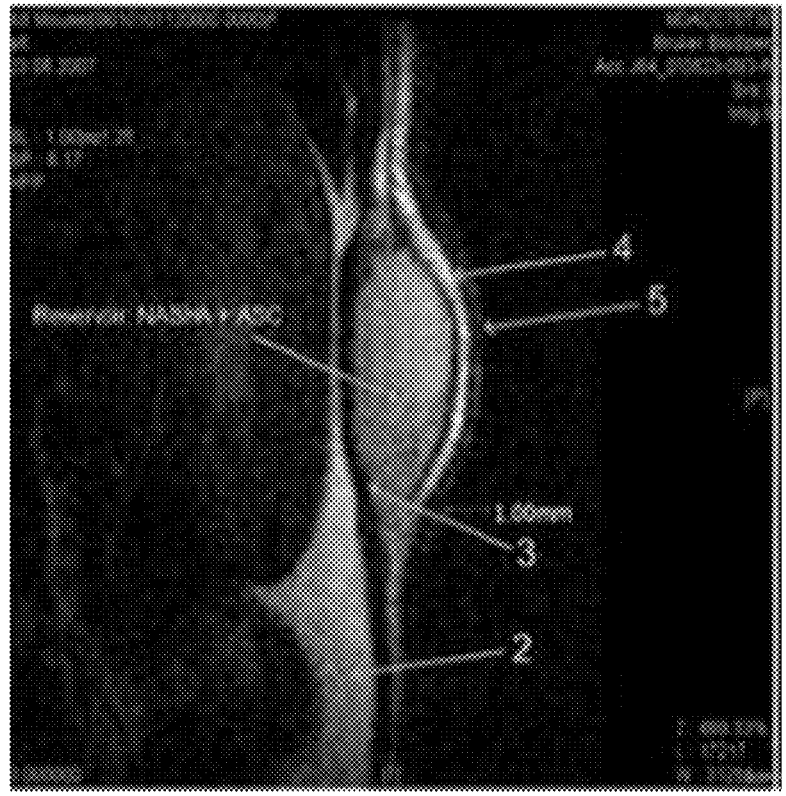

FIGS. 3A-F depict MRI studies of various treatment groups. FIG. 3A depicts no UV treatment/no NASHA treatment. FIG. 3B is UV treatment only, while FIG. 3C is UV/saline treatment. FIG. 3D depicts UV/ADSC treatment, FIG. 3E depicts UV/NASHA only, and FIG. 3F depicts UV/ADSC-NASHA.

Figure 4:
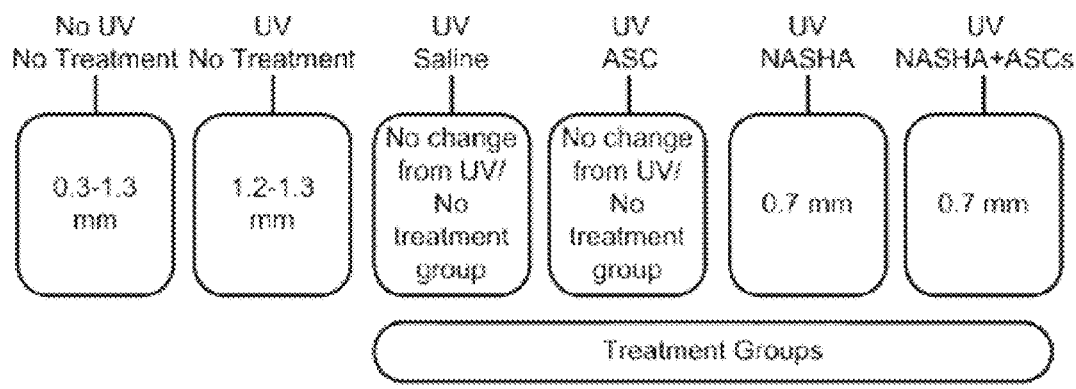

FIG. 4 depicts the measured skin thickness of the various treatment groups shown in FIG. 3A-F.

Figure 5:
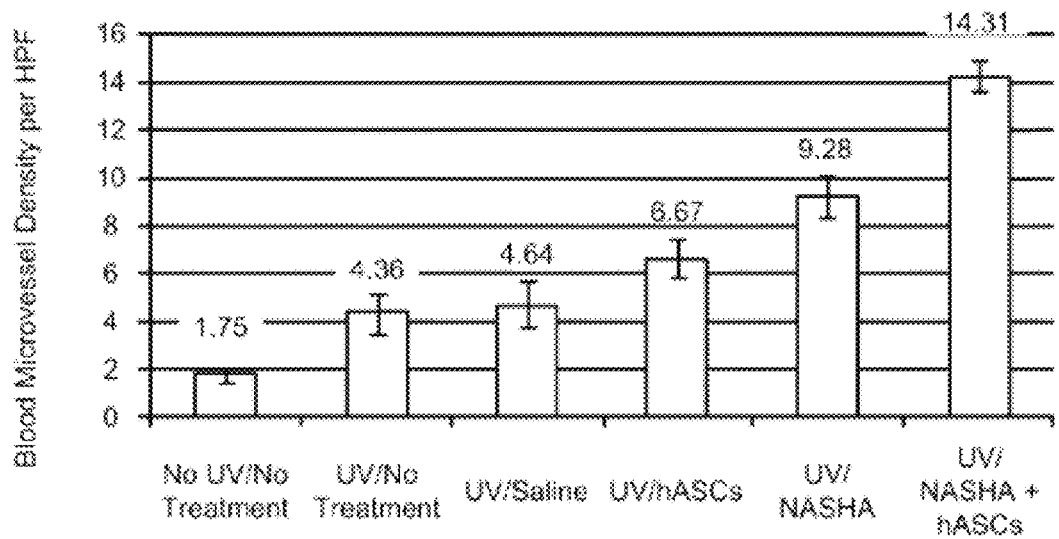

FIG. 5 shows the microvessel density analysis per high-power field of the 6 study groups of FIGS. 3A-F.

Figure 6:
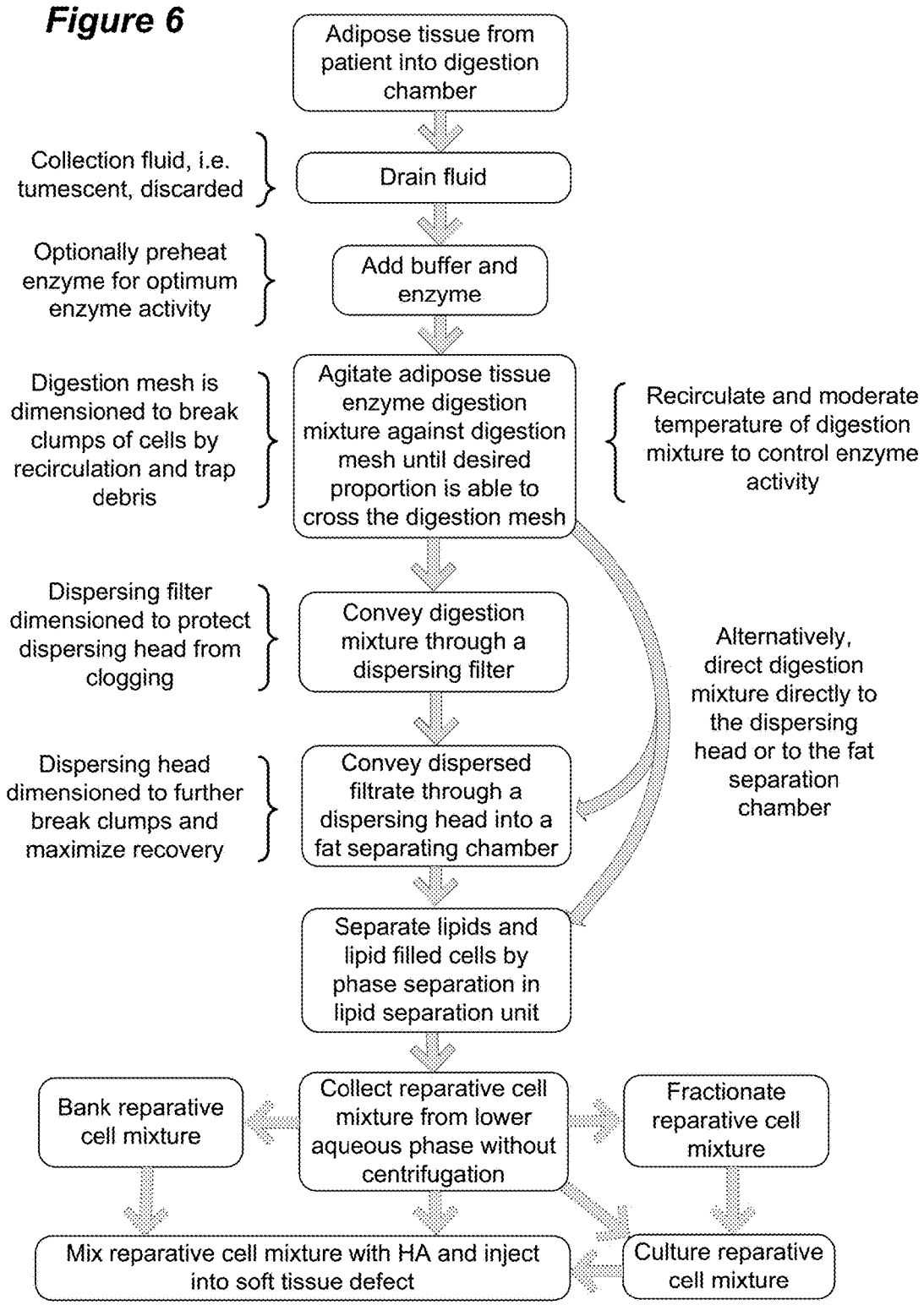

FIG. 6 depicts a flow chart of one embodiment of isolation of fresh reparative cells from adipose tissue.

DETAILED DESCRIPTION OF THE INVENTION

While the making and using of various embodiments of the present disclosure are discussed in detail below, it should be appreciated that the present disclosure provides many applicable inventive concepts that can be employed in a wide variety of specific contexts. The specific embodiments discussed herein are merely illustrative of specific ways to make and use the inventions and do not delimit their scope.

To facilitate understanding of this disclosure, a number of terms are defined. Terms defined herein have meanings as commonly understood by a person of ordinary skill in the relevant arts. Terms such as "a", "an" and "the" are not intended to refer to only a singular entity, but include the general class of which a specific example may be used for illustration. The terminology herein is used to describe specific embodiments, but their usage does not delimit the invention, except as outlined in the claims.

An implant for treatment of human tissue defects that is particularly useful is an autologous transplant of multipotent cells isolated from a tissue that can be removed with little associated trauma to the patient. A mixture of multipotent, early mesenchymal, lineage committed and lineage uncommitted stem/progenitor cells and fully differentiated cells can be obtained from microvessels within many tissues, including adipose tissue. For practical reasons, adipose tissue is a source tissue that is available in most animal and human species without disrupting the physiological functions of the body and with minimal surgical trauma and disfigurement.

Adipose tissue is highly vascularized and is thus a source of endothelial cells, smooth muscle cells, progenitor cells, and of early multipotent mesenchymal stromal cells. Adipose tissue is characterized by the presence of mature adipocytes bound in a connective tissue framework termed the "stroma." In the present invention, stromal cells generally refers to cells resident in the connective tissue of an organ or tissue. The stroma of adipose tissue includes an array of cells that do not include the lipid inclusions that characterize adipocytes. These cells include preadipocytes, fibroblasts, macrophages, monocytes, pericytes, vascular smooth muscle cells, endothelial cells, inflammatory cells such as monocyte/macrophages and lymphocytes, and early undifferentiated mesenchymal stromal (previously termed stem) cells.

Adipose derived stromal cells (ADSCs) are a population of tissue-resident multipotent mesenchymal cells that can differentiate into various lineages when grown in lineage-specific induction medium. ADSCs have certain characteristics similar to those of bone marrow-derived mesenchymal stromal cells (BM-MSCs). Compared with BM-MSCs, isolation of ADSCs is less invasive and yields a high yield per gram of tissue. The isolated ADSC have been shown to have adequate proliferative capacity and have thus been tested for use in tissue repair with promising results suggestive of application for repair of various tissue defects. See Katz, A. J., et al. Emerging approaches to the tissue engineering of fat. *Clin. Plast. Surg.* 26 (1999) 587-603, viii; Safford, K. M., et al. Neurogenic differentiation of murine and human adipose-derived stromal cells. *Biochem. Biophys. Res. Commun.* 294 (2002) 371-379.

In 2005, the International Society for Cellular Therapy (ISCT) stated that the currently recommended term for plastic-adherent cells isolated from bone marrow and other tissues is multipotent mesenchymal stromal cells (MSC) in lieu of the prior "stem cell" term. MSC have been traditionally defined as spindle-shaped or fibroblast-like plastic adherent cells. Although originally isolated from bone marrow, MSC have now been isolated from a variety of tissues including bone periosteum, trabecular bone, adipose tissue, synovium, skeletal muscle, dental pulp and cord blood.

As used herein, the term Mesenchymal Stromal Cell (MSC) means the definition adopted by the International Society for Cellular Therapy and published in a position paper by Dominici et al, *Cytotherapy* 8 (2006) 315. In accordance with the position paper, MSC exhibit:
1) adherence to plastic in standard culture conditions using tissue culture flasks;
2) a specific surface antigen (Ag) phenotype as follows:
   positive ($\geq 95\%+$) for CD105 (endoglin, formerly identified by MoAb SH2), CD73 (ecto 5'nucleotidase, formerly identified by binding of MoAbs SH3 and SH4), CD90 (Thy-1), and
   negative ($\leq 2\%+$) for CD14 or CH11b (monocyte and macrophage marker), CD34 (primitive hematopoietic progenitor and endothelial cell marker), CD45 (pan-leukocyte marker), CD79$\alpha$ or CD19 (B cells), and HLA-DR (unless stimulated with IFN-$\gamma$); and
3) tri-lineage mesenchymal differentiation capacity: able to differentiate in vitro into osteoblasts, adipocytes and chondrocytes in inductive media.

When the connective tissue of adipose tissue is digested, such as with collagenase, the lipid containing adipocytes can be separated from the other cell types. In 1964, Rodbell reported the use of collagenase to dissociate adipose tissue into a cellular suspension that could then be fractionated by centrifugation into an upper, lipid-filled adipocyte fraction, and a cell pellet comprised of non lipid-filled cells. The pelleted non-adipocyte fraction of cells isolated from adipose tissue by enzyme digestion has been termed the "stromal vascular cell" or SVF population. (Rodbell M. "Metabolism of isolated fat cells: Effects of hormones on glucose metabolism and lipolysis" *J. Biol. Chem.* 239 (1964) 375-380).

Heretofore, adipocytes have been separated from the SVF by centrifugation which causes the adipocytes to float and the cells of the SVF to pellet. Typically however, the SVF is subject to further processing and selection, including plastic adherence. The ability of plastic adherent SVF cells to differentiate into multiple lineages fit the criteria of multipotent mesenchymal stem cells. (See review by Zuk et al "Human Adipose Tissue is a Source of Multipotent Stem Cells" *Mol. Biol. Cell* 13 (2002) 4279-95). Cells from the stromal vascular fraction that have been subject to plastic adherence are typically referred to as cultured stromal vascular cells or "adipose tissue-derived stromal cells" (ADSC) and will be referred to as such herein.

Notwithstanding other definitions that may exist in the art, as used herein, the term "stromal vascular fraction" or SVF cells refers to all of the constituent cells of adipose tissue after enzyme digestion and removal of adipocytes and are not limited to plastic adherent cells.

As used herein, "reparative cell population" refers to a mixture of cells that includes "tissue engrafting cells" that are herein defined to include MSC as well as cells such as fibroblasts and endothelial cells that are able to proliferate and engraft a target tissue when returned to the body. The reparative cell population may also include one or more "supportive cell" populations. Supportive cells are herein defined as cells that do not permanently engraft in the target tissue but may aid in the tissue remodeling process that is essential to healing of damaged tissue. These may include, for example, lymphocytes and macrophages. As used herein, the term "reparative cell population" is not limited to plastic adherent cells and may be the same as adipose tissue derived stromal vascular fraction cells under some circumstances.

To date, studies done with autologous transplantation of stem cells, including ADSC have involved cells that have undergone classical stem cell isolation, which involves plastic adherence and culturing through several passages. Application of these plastic adherent adipose derived stromal cells (ADSC) to various matrices has been tested. See e.g. Altman, A. M., et al. Dermal matrix as a carrier for in vivo delivery of human adipose-derived stem cells. *Biomaterials* 29 (2008) 1431-1442; Cowan, C. M., et al. Adipose-derived adult stromal cells heal critical-size mouse calvarial defects. *Nat. Biotechnol.* 22 (2004) 560-567; Lendeckel, S., et al. Autologous stem cells (adipose) and fibrin glue used to treat widespread traumatic calvarial defects: case report. *J. Craniomaxillofac. Surg.* 32 (2004) 370-373; Lu, F., et al. Improved viability of random pattern skin flaps through the use of adipose-derived stem cells. *Plast. Reconstr. Surg.* 121 (2008) 50-58.

While such isolation and culturing may be acceptable and even desirable under certain circumstances, several treatment procedures are required including at least one harvest procedure and at least one later implantation procedure. Potential disadvantages to culturing of cells include the possibility for contamination and introduction of adventitious agents from necessary culture medium. Anther disadvantage, as will be discussed later, is the potential loss of large numbers of useful cells that do not exhibit plastic adherence within 24 hours of isolation. Thus, in one embodiment of the present invention, fresh SVF cells are used in lieu of plastic adherent stromal cells. Such SVF cells are isolated at the point of care, mixed with the media that provide structural support and a favorable environment for growth, and reinjected into the patient to fill tissue defects.

The present inventors have sought to identify compositions that provide structural support and a favorable environment for growing cells as a key element for tissue engineering. To explore the role of ADSCs in soft-tissue repair, the present inventors investigated the ability of ADSCs to proliferate and differentiate when integrated ex vivo into an injectable matrix and then injected into a tissue lesion. Effects of addition of the ADSC were compared with the injectable matrix alone. One such identified composition contains hyaluronic acid (HA) and derivatives thereof (HAD).

Hyaluronic acid (HA) is a linear non-sulfated glycosaminoglycan composed of repeating disaccharide units of D-N-acetylglucosamine and D-glucoronic acid linked together via alternating β-1,4 and β-1,3 glycosidic bonds. HA can be 25,000 disaccharide repeats in length such that naturally occurring polymers can range in size from 5,000 to 20,000,000 Da. The average molecular weight of HA in human synovial fluid and purified from human umbilical cord is 3-4 million Da. HA is a natural component of the extracellular matrix of the dermis and other soft tissues. Used as cosmetic fillers, certain HA derivatives have proven well tolerated with persistent volume fill up to 6 months. See Carruthers, A., Carruthers, J. Non-animal-based hyaluronic acid fillers: scientific and technical considerations. *Plast. Reconstr. Surg.* 120 (2007) 33S-40S; Fagien, S., Klein, A. W. A brief overview and history of temporary fillers: evolution, advantages, and limitations. *Plast. Reconstr. Surg.* 120 (2007) 8S-16S; and Wang, F., et al. In vivo stimulation of de novo collagen production caused by cross-linked hyaluronic acid dermal filler injections in photodamaged human skin. *Arch. Dermatol.* 143 (2007) 155-163.

As used herein, the term "hyaluronic acid" includes hyaluronic acid (HA) that is isolated from higher organisms as well as HA produced by recombinant means in lower eukaryotes and prokaryotes. The term "hyaluronic acid derivatives" (HAD) means HA from any source that has been further modified, including by crossing linking. One example is RESTYLANE® brand crosslinked hyaluronic acid, which is produced recombinantly by cloning the coding sequence for human hyaluronic acid into Streptococcus and expressing the product therefrom. The RESTYLANE® brand recombinant hyaluronic acid is purified and chemically crosslinked with BDDE, stabilized and suspended in phosphate buffered saline at pH 7.0 as described in U.S. Pat. No. 5,827,937 (assigned to Q-Med AB). Products such as the RESTYLANE® brand crosslinked hyaluronic acid have been referred to as non-animal stabilized hyaluronic acids (NASHA). Other hyaluronic acid derivatives that are commercially available and FDA approved for human cosmetic use include PERLANE® (a larger gel particle form NASHA produced by the makers of RESTYLANE) and the JUVEDERM® brand NASHA gel (Allergan), which is reported to be more extensively crosslinked than the RESTYLANE brand NASHA.

The Durolane® brand NASHA gel (Q-Med AB, Uppsala, Sweden) is highly crosslinked recombinantly produced human hyaluronic acid that is approved in Europe for treatment of osteoarthritis of the knee and hip by single injection to the joint space. Other hyaluronic acids are approved for treatment of osteoarthritis by multiple injections into the joint space. The first such approved products, the ARTZ®, ARTZAL® and SUPARTZ® brands of HA (Seikagaku Corp.) are native hyaluronans having a relatively high-molecular-weight in the range of 0.5-1 million daltons. In contrast, the Synvisc® (Genzyme) HA product for intra-articular injection is isolated from chicken combs but is cross-linked resulting in an increased molecular weight over native isolated hyaluronans. The stabilized or cross-linked HA typically have improved elastoviscous properties and a longer in vivo retention time than non-stabilized HA.

Given its hygroscopic properties and putative ability to provide a mechanical stimulus to dermal fibroblasts for the promotion of collagen I synthesis, NASHA have been hypothesized to confer temporary volume-filling effects. See Wang, F. et al. supra. ADSCs have also been shown by certain of the present inventors to be consistently positive for the surface marker CD44, which is the binding ligand for hyaluronic acid. See Bai, X., et al. Electrophysiological properties of human adipose tissue-derived stem cells. *Am. J. Physiol Cell Physiol* 293 (2007) C1539-C1550. Such a ligand-substrate interaction is implicated in downstream cascades tied in with stem cell differentiation. Furthermore, certain of the present inventors have shown that some of the injected ADSCs in the NASHA environment express an HSP-47 positive phenotype (data not shown). It is known that HSP-47 positive cells produce collagen I, which is a key factor for persistent volume fill over time. See Wang, F. et al. supra.

The cellular preparations disclosed herein can be applied to subjects for various cell therapeutic purposes. Such cell therapies generally refer to the regeneration and/or repair of injured or diseased tissue. Non-limiting examples include wound healing (infected and non-infected), bone fracture healing, treatment of non-healing ulcers, fistulas, hernia repair, tendon repair, plastic surgical indications including skin grafting, breast augmentation and reconstruction, cartilage regeneration, including cartilage of the nose and pinna of the ear, engraftment after chemotherapy, rescue of retinal degeneration, treatment of ischemic disease (e.g., ischemic heart disease and peripheral arterial disease), treatment of nerve injury, filling of heart aneurysms and of the atrial appendage, creation of an artificial bladder and bladder wall repair, repair and reconstruction of intestines, and repair and reconstruction of vessels and associated structures.

In one embodiment of the invention, HA or HAD together with a regenerative cell population are utilized to provide tissue augmentation and to generate a long lasting mechanical and function filling of the tissue structures responsible for bladder control in the treatment of urinary incontinence (UI). Administration of HA or HAD with a regenerative cell population may be performed by ultrasound guided transurethral injection into the submucosal tissue at the neck of the bladder to result in filling or bulking to treat UI. Additionally or alternatively, regenerative cells with capacity for myogenic or neurogenic repair may be administered in combination with HA or HAD via EMG guided transurethral injection into the rhabdosphincter at the neck of the bladder to enhance muscular tone of the sphincter and/or neural control. These combination treatments would provide enhanced durability versus filler alone, and in addition, the regenerative cell component would directly address the underlying tissue loss and neuropathies that lead to UI.

In one embodiment in this and other contexts of soft tissue repair for a multitude of tissues and organs, other biological fillers such as collagen agents (e.g., Contigen®, C.R. Bard Corp., Covington, Ga.) are added to the formulation prior to administration. Use of regenerative cells in combination with collagen filling agents will provide similar therapeutic effects to those described for the combination of regenerative cells with HA and HAD. In addition, because cells within the regenerative cell preparation have anti-inflammatory properties, combining the regenerative cells with collagen filler may be used to reduce the incidence and or severity of host inflammatory response to the collagen filler. A host inflammatory response is known to occur in a subset of patients treated with collagen fillers and restricts their use from patients that exhibit a positive skin test prior to treatment.

EXAMPLE 1

To explore the potential for a role for SVF cell in soft-tissue repair, the present inventors investigated the ability of the ADSC subset of SVF cells to proliferate and differentiate when exposed to hyaluronic acid compared with growth of ADSC under standard culture conditions. It was also investigated whether the mixture had a collagen-inducing effect in vitro.

As disclosed herein, the present inventors have demonstrated that a commonly used injectable soft-tissue NASHA filler is compatible with tissue-resident MSCs derived from adipose tissue. The ADSCs were shown to proliferate equally when grown on HA or NASHA substrates compared to standard tissue culture-conditions on a plastic substrate. Real-time PCR showed that procollagen gene expression is increased in ADSC cultures in conjunction with HA. Importantly, in vivo studies showed a significant increase in vascular density at the site of ASC-NASHA grafts was shown as compared with NASHA alone. A robust vascular supply is critical for the establishment of the interface between graft and native tissue, which allows the ingrowth of native tissues in order to maintain a long-term fill effect of such injectable grafts.

MSC isolation from Adipose Tissue Stroma and Cell Culture: Fresh adipose tissue-resident stromal cells (ADSC) were obtained from human liposuction aspirates obtained after informed consent from patients undergoing elective lipoplasty. The mean donor age was 39.9 years, and the mean body mass index was 27.6. Fluid was removed from the lipoaspirate, and the tissue was subjected to a mixture of collagenase and neutral protease in sterile, isotonic buffer with subsequent incubation for 30 minutes at 37° C. with agitation. After incubation, free lipid, adipocytes, and debris were removed using a combination of filtration and differential sedimentation. Cells were finally suspended in 10 milliliters (ml) of α-minimum essential medium (MEM) containing 20% fetal bovine serum (FBS), 2 mM L-glutamine, 100 U/ml penicillin and 100 µg/ml streptomycin. This suspension was placed into T75 flasks and incubated at 37° C. in a humidified chamber containing 5% $CO_2$ for 24 hours. Subsequently, the non-adherent cells and debris were discarded, and adherent cells were then expanded in culture with media changes at three day intervals. ADSCs prepared via similar techniques have previously been demonstrated to be capable of multi-lineage differentiation in the inventor's laboratories. Culture-expanded cells at passage 1 through 8 were used for all experiments.

GFP Transfection: In order to follow the fate of the cells, especially for in vivo studies, ADSCs at 60% confluence were transfected with a lentiviral vector carrying enhanced green fluorescent protein (eGFP) under the control of a CMV promoter using an adaptation of standard protocols. Briefly, $1.0 \times 10^6$ ADSCs at passage one were incubated in a 10 ml aliquot of vector-containing medium ($1.2 \times 10^6$ virus particles/ml medium) in a 75 $cm^2$ flask. 8 µg of polybrene was added (Sigma-Aldrich, St. Louis, Mo., USA). Vector-containing medium was subsequently replaced by fresh medium 24 hours later. Six days subsequent to infection, transfected and culture-expanded GFP-positive cells were subjected to flow cytometric sorting with stringent gating for successfully-transfected fluorescent cells using the FACSVantage SE cell sorter (Becton Dickinson, Franklin Lakes, N.J., USA).

ADSC-Hyaluronic Acid Compatibility Studies: Human ADSCs were suspended in hyaluronic acid (H1504; Sigma Aldrich, St. Louis, Mo., hyaluronic acid potassium salt isolated from human umbilical cord) at a concentration of $1 \times 10^6$ cells/100 µl. The suspension was kept under ambient conditions in a 1 ml syringe for 30 minutes in order to replicate clinical conditions that a similar preparation might experience in transit between preparation and application in the operating theater. Subsequently, the ADSC-hyaluronic acid suspension was passed 2 times through a 27-gauge needle, and returned to standard culture conditions.

ADSCs suspended in hyaluronic acid and subsequently placed under culture conditions maintained a typical spindle-shaped morphology. The cells grew with normal kinetics in vitro and continued to express GFP as indicated by fluorescent microscopic examination, which demonstrated the compatibility of ADSCs to grow after mixing with hyaluronic acid, with no sign of a cytotoxic or other adverse impact on normal cell growth and expansion in culture.

Proliferation Studies: The cell proliferation assay was a BrdU ELISA (calorimetric) kit (Roche, Rotkreuz, Switzerland), used per the manufacturer's protocol. All experiments were carried out in the 96-well plate format. Experimental wells were covered with a thin layer of 20 mg/ml non-animal stabilized hyaluronic acid (NASHA) at pH 7.0 by injection of 50 µl aliquots into the well and distribution by even spreading with an 18 gauge needle tip. For this assay, the RESTYLANE® brand of lightly crosslinked human recombinant hyaluronic acid was utilized. (RESTYLANE®, Q-Med AB, Uppsala, Sweden).

Briefly, ADSCs at passage 6 were plated over the NASHA at a density $1.0 \times 10^4$ cells/well in a volume of 100 µl and incubated for 12 hours in a humidified chamber containing 5% $CO_2$ at 37° C. BrdU labeling solution was added for a labeling time of 2 hours, placed in a fixation/denaturation solution and incubated at room temperature for 30 minutes, followed by 90 minute incubation in anti-BrdU-peroxidase antibody. Finally, samples were placed in substrate solution for 5-30 minutes (until color development sufficient for photometric detection), 1M $H_2SO_4$ was added, and absorbance at 450 nm was measured on an ELISA plate reader (reference wavelength 690 nm).

The mean relative absorbance at 450 nm for ADSC cultured on NASHA was 1.15±0.22, whereas the proliferation for control ADSCs grown on tissue-culture plastic was found to be 1.19±0.06. Results indicate that NASHA has no negative effect on ADSC proliferation, consistent with the compatibility results obtained after treatment with hyaluronic acid.

Scanning Electron Microscopy: For SEM, passage 4 human ADSCs were seeded at a density of $2.0 \times 10^4$ cells/well in a 6-well plate format. Glass coverslips were used as a control while glass coverslips coated with 100 µl of hyaluronic acid and then air-dried were utilized for experimental samples. Cells were cultured in a humidified chamber containing 5% $CO_2$ at 37° C. for 72 hours, and then fixed and processed. Adaptations of established methods were used to perform SEM.

Figure 1A:
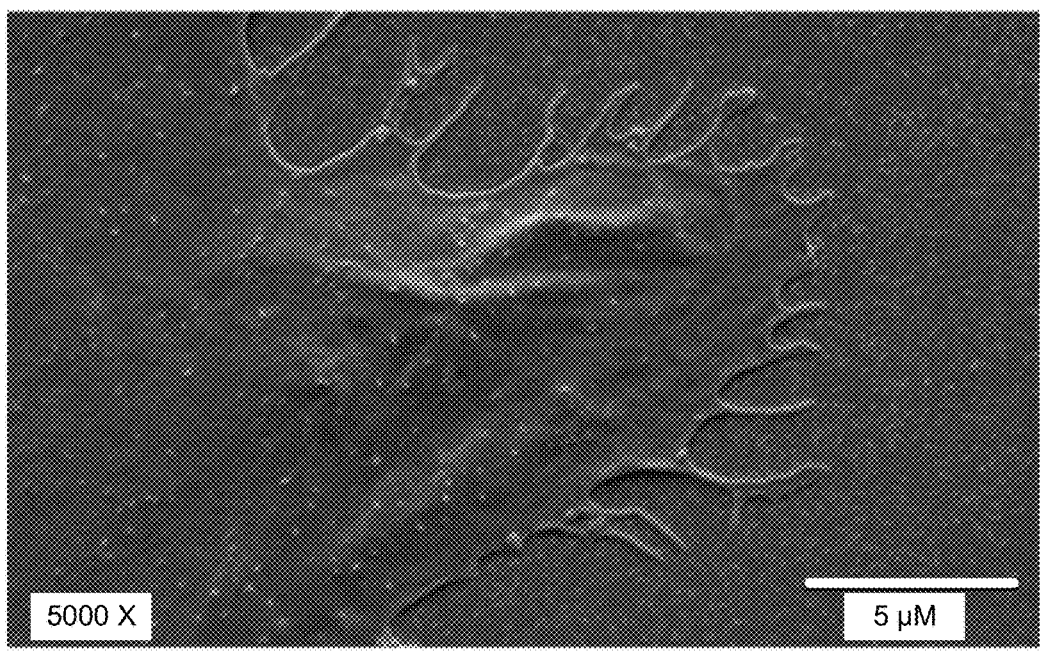
FIG. 1A shows SEM photomicrographs of adipose derived stromal cells (ADSC) growing on a control glass surface.
Figure 1B:
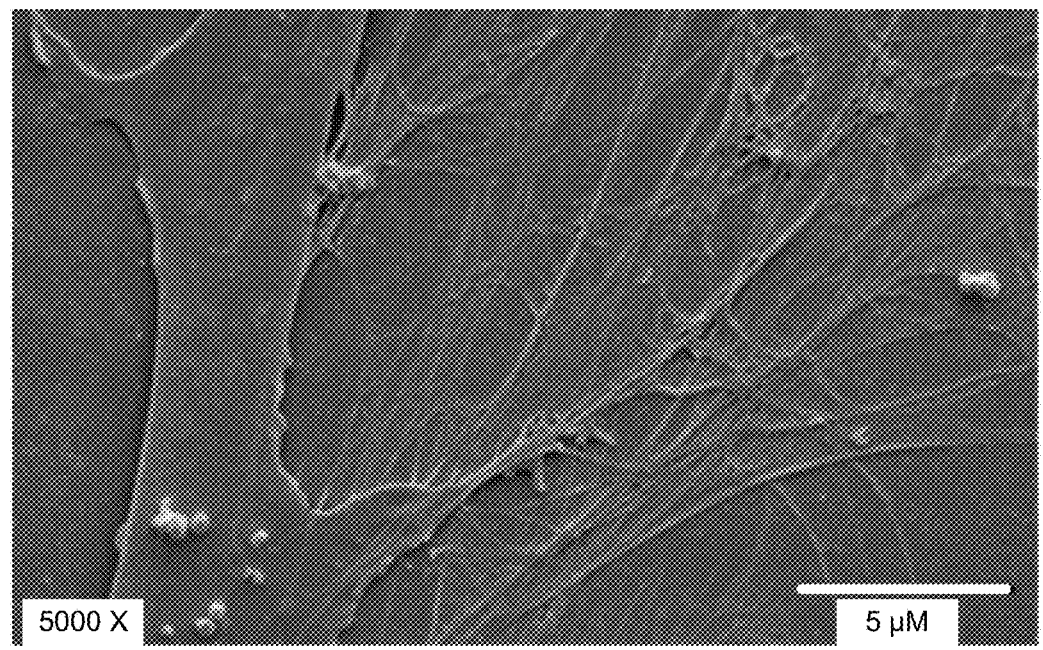
FIG. 1B shows the more complex structures formed by ADSC growing on a hyaluronic acid coated substrate.

SEM examination of interfaces between ADSC and the hyaluronic acid (HA) cell substrate revealed a markedly increased frequency of complex microvillus networks in the case of HA-seeded ADSCs (FIG. 1B) versus in controls grown on glass coverslips (FIG. 1A). HA-seeded ADSCs demonstrated a complex lattice-like pattern of microvilli acting as a collective anchorage network with enhanced surface area interfacing the substrate. These regions were not observed among control ADSCs seeded on glass or plastic surfaces and maintained under identical culture conditions.

Real-Time Polymerase Chain Reaction: To determine the effect of HA on procollagen mRNA expression by ADSC, mRNA was extracted from 80% confluent passage 3 human ADSCs cultured on HA-coated flasks after 3 days, using an RNAqueous Kit (Ambion). cDNA was synthesized from 1 µg of mRNA using SuperScript II reverse transcriptase (Ambion), in accordance with the manufacturer's instructions. cDNA samples were subjected to PCR amplification using AccuPrime Super Mix I (Invitrogen) with specific primers for several human procollagens and related enzyme Prolyl 4 Hydroxylase as well as the housekeeping gene 36B4. Real Time-PCR was performed with a BioRad MyIQ/ICycler.

Real-time PCR results for gene expression of human procollagen 1 α 2, procollagen 3 α 1, and prolyl 4 hydroxylase from ADSCs seeded on NASHA demonstrated a significant ~170-fold increase in procollagen 1 alpha 2 gene expression. Procollagen 3 α 1 and prolyl 4 hydroxylase expression also increased, by 2.58- and 1.97-fold, respectively.

In Vivo Photoaging Model and ADSC-HA Therapy: An in vivo model of photoaging was utilized that involved exposing 6-week-old male nu/nu mice to narrow-band UVB at 30 min intervals 5 times weekly for 10 weeks, resulting in a characteristic photoaged morphometric result. A total of 21 mice were used in accordance with IACUC guidelines and approval. Mice in the photoaged group (n=18) were randomized to receive 1 of 6 different treatments (self-controlled by different bilateral injections): ADSC/PBS; NASHA/PBS; ADSC-NASHA/PBS; ADSC/NASHA; ADSC/ADSC-NASHA; ADSC-NASHA/ADSC. Non-photoaged control mice (n=3) received the following interventions: PBS, NASHA/PBS, and ADSC-NASHA/PBS.

For therapeutic injections, 100 µl of PBS was delivered for PBS control treatments, and an equal volume of NASHA and ADSCs suspended in NASHA was used in the respective treatment groups. After mice were randomized to the treatment groups, injections were delivered via 27-gauge needle into the deep intradermal and subcutaneous cutaneous compartments. For the ADSC-NASHA preparation, ADSCs were trypsin dissociated from T75 tissue-culture flasks at a confluence of 90%, and pelleted via centrifugation (1500×g) before resuspension in NASHA at a density of $1.0 \times 10^6$ cells/100 µl. Resuspension was achieved by mixing with a sterile spatula in 50 ml conical centrifugation tubes. ADSC-NASHA was subsequently loaded into the back of 1 ml tuberculin syringes fitted with 27 G needles. Mice were examined daily after injections, and digital images were taken for 3 weeks post treatment to document the gross effects of therapy in the setting of photoaging.

Representative mice in each treatment group were subjected to magnetic resonance imaging (MRI) before treatment and after 3 weeks using a Tesla Biospec small-animal imaging system, Bruker BioSpin, Rheinstetten, Germany. Mice were subsequently euthanized at 3 weeks after treatment, and the treatment sites collected for histology. For immunohistochemical testing, primary antibodies specifically directed against the following epitopes were used to trace the fate of the ADSCs: Green Fluorescent Protein (αGFP ab6556; 1:200 dilution), Ki67 (ab833 and ab15580; 1:50 dilution), vWF (A0082; 1:100 dilution), and collagen 1 (SC-8784; 1:50 dilution). Ki67 antigen is the prototypic cell cycle related nuclear protein, expressed by proliferating cells in all phases of the active cell cycle (G1, S, G2 and M phase) but is absent in resting (G0) cells. For microvessel density quantification, paraffin sections were deparaffinized and stained with primary antibody directed against von Willebrand Factor (vWF; 1:100 dilution, polyclonal rabbit-anti-human, Dako, Glostrup, Denmark). Statistical analysis was conducted using Statistical Program for Social Science (SPSS) for Windows (SPSS Inc., Chicago, Ill.). Student's t-test and ANOVA was used to determine the statistical significance of data. Values are depicted as means±SD, with a P value≤0.05 considered statistically significant.

Physical examination of UV-B treated mice after treatments for 3 weeks revealed rhytides (wrinkles) in the control groups treated with UVB only, as well as in the PBS and ADSC-treated groups. However, in mice treated with both NASHA and ADSC-NASHA, a consistent and persistent ablation of photoinduced rhytides was observed. The extent and quality of this ablation was not significantly different between NASHA versus ADSC-NASHA. Gross rhytid effacement was associated with a clear, demarcated region of focal volume fill consistent with filler injection at the treatment site. There was no significant diminution of volume or change in contour at treatment sites in either NASHA or ASC-NASHA-treated mice with time over the 3-week course of the experiment.

MRI findings showed a reduction in hypodermal photoinduced hyperplasia in the ADSC-NASHA treatment group compared with controls. Index scan analysis of representative mice from the 6 study groups indicated marked hyperplasia from baseline (FIG. 2A) after treatment with UVB irradiation (FIG. 2B). Note the thin white dermal layer (*) in FIG. 2A versus the hyperplasia of white dermal layer (**) in FIG. 2B. No significant differences between the treatment site and surrounding tissue were observed in mice treated with UV and ADSC alone and the injection site of ADSCs alone was not recognizable after 3 weeks.

For both NASHA and ADSC-NASHA grafts, the MRI study revealed the superficial and deep graft borders to be smooth and well circumscribed (FIGS. 3A-F). FIG. 3A depicts no UV treatment/no NASHA treatment. FIG. 3B is UV treatment only, while FIG. 3C is UV/saline treatment. FIG. 3D depicts UV/ADSC treatment, FIG. 3E depicts UV/NASHA only, and FIG. 3F depicts UV/ADSC-NASHA. In these Figures, 1=Kidney, 2=Perirenal fat, 3=Abdominal wall musculature, 4=Hypodermis, 5=Dermis.

Representative graft sites appeared to be encapsulated. The interior structure of the grafts appeared to be homogenous at both the NASHA and ADSC-NASHA treatment sites. The intensity of both graft types had signal characteristics consistent with a largely aqueous tissue. After treatment with both NASHA and ADSC-NASHA, a reduction in hypodermal diameter was observed compared with that in pre-treatment baseline scans and compared with skin regions adjacent to the graft injection sites. Skin thickness in the control groups ranged from 0.3 to 1.3 mm, whereas both the NASHA and ADSC-NASHA groups had a 0.7 mm thickness after treatment, leaning toward a decrease in skin thickness superficial to the injection site (FIG. 4). This phenomenon was most conspicuously noted superficial to the maximum diameter of the graft, consistent with the gross observation of rhytid ablation in the immediate region of graft injection sites.

Histological testing in the ADSC-NASHA group showed ADSC engraftment, proliferation, and collagen production. Hematoxylin-eosin-stained sections revealed clearly demarcated regions for both NASHA and ADSC-NASHA graft fill. Close examination of graft sites revealed the typical network of deep violet hematoxylin-staining NASHA fibers. Control ADSC alone and saline injection sites showed no marked differences in tissue architecture and cellular composition compared with surrounding tissue. Features of photoaging (epidermal hyperplasia and elastosis) were observed among the cutaneous strata in all specimens. Within the ADSC-NASHA-treated group, a clear presence of fibrovascular tissue was observed to variable degrees into and among the NASHA strands. Associated cells appeared to have a spindle-like morphology and to variably occupy either single or stratified layers of cell advances along NASHA strands, at times forming nests of cells growing in association with the graft network.

Immunohistochemistry results indicated as well that ADSCs had engrafted successfully in 3-week tissue biopsies from ADSC-NASHA-engrafted mice, and samples showed signs of incorporation into the NASHA filler, forming island-like NASHA strands surrounded by ADSCs and other cells.

GFP signal positivity in immunofluorescence results indicated that ADSCs engrafted successfully in 3-week tissue biopsies in the ASC-NASHA group and that they coexpressed GFP with collagen 1, Ki67, vWF and HSP-47 (Heat Shock Protein-47). As a negative control, specimens with only NASHA showed no signal for GFP. The GFP-positive cells observed in ADSC-NASHA biopsies among the cellular elements of fibrovascular invasion fronts were noted to infiltrate and incorporate into the NASHA element of the graft on hematoxylin-eosin staining and immunohistochemical examination.

Significantly increased microvessel density was observed when ADSCs are included with the NASHA filler. The vascular density of peri-implant dermal elements was higher in the ADSC-NASHA group than in the NASHA only group. The mean vascular density in NASHA specimens was 9.28±0.91 microvessels/high-power field, whereas that in ADSC-NASHA was 14.31±0.59 microvessels/high-power field (P<0.01) (FIG. 5).

EXAMPLE 2

It has been shown that the phenotype of plastic adherent adipose derived cells changes with cell culture and is influenced by culture conditions. (Gimble J and Guilak F. "Adipose-derived adult stem cells: isolation, characterization, and differentiation potential" *Cytotherapy* 5(5) (2003) 362-369; Boquest A C, et al "Isolation and transcription profiling of purified uncultured human stromal stem cells: Alteration of gene expression after in vitro cell culture" *Mol. Biol. Cell* 16(3) (2005) 1131-1141). Use of reparative cell preparations such as freshly derived SVF populations for incorporation into HA fillers would avoid the need for culture with its attendant disadvantages and would permit utilization of larger cell numbers including cells that would ultimately exhibit the properties of plastic adherent stem cells if given the chance but are discarded using standard stem cell isolation procedures that call for the discard of all cells that are not adherent at 24 hours of culture.

The present embodiment may be utilized in a process for the isolation of cell populations without loss of cells that would otherwise be useful but lack a property of being strongly adherent when first removed from the body. For example, when plated onto plastic, adherence of non-fibroblast cells in a fresh cell preparation may require several hours to more than one day. Culture of the fresh cell preparation changes two characteristics. First, monolayer culture selectively enhances certain cell populations resulting in a cell preparation that is distinct from the fresh isolate. Second, culture in an adherent monolayer selects and conditions the cells for adherence, so that upon passaging and replating the resulting cell populations adhere much more rapidly (i.e., <30 min). Isolation of MSC involves plastic adherence by definition and eliminates non-adherent and weakly adherent cells in spite of their beneficial properties.

Desirably, use of reparative cell preparations for cell therapy without prior expansion in cell culture, involves obtaining a sufficient number of cells for therapeutic use without expanding the cells in culture. Subcutaneous tissue may provide as many as 300,000 reparative cells per gram, which have an appropriate cell type composition. In contrast to the prevailing view that a single cell type is optimal for cell therapy, the present inventors believe that multiple cell types are able to act in a coordinated manner to achieve healing and/or repair and may be desirable in certain situations. Thus, in one embodiment a heterogeneous reparative cell population is provided to mediate a tissue healing and repair process that emulates endogenous repair.

In contrast to use of plastic adherent ADSC, the present embodiment provides for isolation of reparative cell populations without the use of centrifugation or plastic adherence, and which is suitable for use at the point of care. In one example, depicted in a flow chart in FIG. 6, a reparative cell population has been isolated as follows. Lipoaspirate was collected under informed consent in the operating room directly into a unitary purification apparatus by standard suction assisted lipoplasty with tumescent. The apparatus including tumescent fill was transported to the laboratory and processed within 2 hours of collection. In practice however, it is anticipated that the purification apparatus will be suitable for, and may be used, in the operating suite. The digestion chamber of the apparatus included a predigestion chamber and an inner postdigestion chamber separated by a nylon mesh having a pore size of approximately 1 mm. The tumescent was drained and a volume of approximately 100 ml of drained lipoaspirate was washed by draining the predigestion chamber and refilling with a solution of lactated Ringer's solution, which was prewarmed to 37° C. containing a proteolytic enzyme combination comprised of collagenase IV (60,000 U) and dispase (120 U).

A digestion recirculation loop was implemented by a pump actuated flow path from the predigestion chamber into the postdigestion chamber and including passage across a heat exchanger that maintained the digestion mixture at approximately 37° C. Recirculation was continued for approximately 30 to about 60 minutes or until greater than 90% of the cellular volume of the predigestion chamber was able to pass the 1 mm mesh into the post digestion chamber. The design of the pre and post digestion chambers, separated by the nylon mesh across which the recirculation flow path passes repeatedly, provided trapping of connective and other debris tissue on the digestion mesh. After digestion was sufficiently complete, the digestion mixture was pumped tangentially over a nylon dispersing filter having a pore size of 250 μm. The filtered digestion mixture was then pumped into a columnar lipid separating chamber that was integral to the apparatus. The filtered digestion mixture entered the lipid separating chamber through a dispersing head having a plurality of downwardly directed pores with a pore size of 500 μm and disposed proximally to a bottom inner surface of the lipid separating unit. The design was adapted for forcibly flowing the cell mixture against an inner surface within the lipid separating unit and thereby further disrupting cell clusters within the cell mixture prior to fluid phase separation. The lipid separating chamber was prefilled with a volume of 150 ml lactated Ringer's solution prior to introduction of the digestion mixture such that when the filtered digestion mixture entered the chamber, any clusters of cells, including lipids or adipocytes, were subject to fluid shear as the lipid moieties float upward in the aqueous solution. Fluid phase separation was allowed to proceed at room temperature for about 5 to about 30 minutes prior to collection of the stromal vascular fraction from the bottom of the lipid separating chamber.

In comparing the cells isolated as disclosed herein with mesenchymal stromal cells isolated using centrifugation and plastic adherence in accordance with conventional preparation methods, several notable differences are apparent. Mesenchymal stromal cells have been classically isolated from adipose tissue using enzymatic digestion, centrifugation to remove lipid filled cells and plastic adherence with culture in vitro. These cells show a fibroblast-like morphology. Although the cells are initially heterogeneous, the phenotype of population changes in culture including loss of CD31+, CD34+, CD45+ cells, and an increase in CD105 and other cell adhesion type molecules. Generally, <10% of the cells express markers associated with stemness (e.g., CXCR4, Oct-4, sca-1, SSEA-4) and a substantial fraction differentiates into adipocytes in inductive media. A lesser fraction differentiates into other lineages (bone, cartilage, nerve) in inductive media.

The reparative cell population isolated as disclosed herein without centrifugation or plastic adherence is also a heterogenous population and generally <10% express markers associated with stemness (e.g., CXCR4, Sca-1, SSEA-1, SSEA-4, VEGFr2, CD117, CD146, Oct4). However, a substantial fraction of the early multipotent stem cells are not plastic adherent. Importantly, a substantial fraction of cells expressing markers of stemness, endothelial cell lineages and/or exhibiting a small diameter 6 mm) are not adherent and are lost using conventional isolation methods that rely on plastic adherence or centrifugation.

Use of freshly isolated reparative cell populations, incorporated into HA or HAD containing solutions and injected into tissue defects allows for a large number of fresh cells to be injected and avoids the need to culture the cells, which may introduce undesirable adventitious agents.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

We claim:

1. A method of preparing and administering, at a point of care, an injectable cell graft for treating or preventing urinary incontinence comprising:

isolating an autologous stromal vascular fraction (SVF) cell preparation from an adipose tissue of a mammal by releasing cells from a connective tissue matrix of the adipose tissue and substantially removing debris and adipocytes without subjecting the autologous SVF cell preparation to expansion in culture and without subjecting the autologous SVF cell preparation to plastic adherence; and injecting or implanting the autologous SVF cell preparation into a bladder tissue at the point of care without culturing of the autologous SVF cell preparation.

2. The method of claim 1, wherein, prior to injecting or implanting, the autologous SVF cell preparation is combined with a biological filler that comprises one or more of hyaluronic acid (HA), a hyaluronic acid derivative (HAD), and a collagen agent.

3. The method of claim 1 wherein the autologous SVF cell preparation is exposed to inductive media prior to injection.

4. The method of claim 3, wherein the inductive media is adapted to induce differentiation of cells in the SVF cell preparation into one or more cell lineages including adipocytes, chondrocytes, endothelial cells, hepatocytes, myoblasts, neurons, and osteoblasts.

5. The method of claim 1, wherein the autologous SVF cell preparation is administered by a transurethral injection.

6. The method of claim 5, wherein the injection is into a submucosal tissue at a bladder neck to fill or bulk the bladder tissue at the bladder neck.

7. The method of claim 5, wherein transurethral injection is into a rhabdosphincter bladder tissue to enhance muscular tone and/or neural control of the rhabdosphincter bladder tissue.

8. The method of claim 1, wherein more than 3% and up to 10% of cells in the cell preparation express markers associated with stemness.

9. The method of claim 8, wherein the markers associated with stemness include one or more of CXCR4, Oct-4, sca-1, SSEA-4, VEGFr, CD146, and CD117.

10. The method of claim 2, wherein the hyaluronic acid derivative (HAD) comprises a cross-linked hyaluronic acid.

11. A method of preparing and administering an injectable cell graft for treating or preventing urinary incontinence in a patient in need thereof comprising:

isolating an autologous stromal vascular fraction (SVF) cell preparation from an adipose tissue of the patient by releasing cells from a connective tissue matrix of the adipose tissue and substantially removing debris and adipocytes without subjecting the autologous SVF cell preparation to expansion in culture and without subjecting the autologous SVF cell preparation to plastic adherence; and injecting or implanting the autologous SVF cell preparation into a bladder tissue of the patient without culturing of the autologous SVF cell preparation.

12. The method of claim 11, wherein, prior to injecting or implanting, the autologous SVF cell preparation is combined with a biological filler that comprises one or more of hyaluronic acid (HA), a hyaluronic acid derivative (HAD), and a collagen agent.

13. The method of claim 11 wherein the autologous SVF cell preparation is exposed to inductive media prior to injection.

14. The method of claim 3, wherein the inductive media is adapted to induce differentiation of cells in the SVF cell preparation into one or more cell lineages including adipocytes, chondrocytes, endothelial cells, hepatocytes, myoblasts, neurons, and osteoblasts.

* * * * *